(12) United States Patent
Kooiman

(10) Patent No.: US 6,299,439 B1
(45) Date of Patent: Oct. 9, 2001

(54) SUTURE EXPANSION DEVICE

(76) Inventor: Johan Anton Kooiman, 's-Gravenbroekseweg 99, NL-2811 GD Reeuwijk (NL)

( * ) Notice: Subject to any disclaimer, the term of this patent is extended or adjusted under 35 U.S.C. 154(b) by 0 days.

(21) Appl. No.: 09/559,485

(22) Filed: Apr. 27, 2000

(30) Foreign Application Priority Data

Jan. 7, 2000 (NL) .................................................. 1014043

(51) Int. Cl.[7] .................................................. A61C 3/00
(52) U.S. Cl. .................................................. 433/7
(58) Field of Search .................................................. 433/7

(56) References Cited

U.S. PATENT DOCUMENTS

| | | | |
|---|---|---|---|
| 3,454,001 | * | 7/1969 | Stockfisch .................. 433/7 |
| 4,462,799 | * | 7/1984 | Nardella ..................... 433/7 |
| 5,439,377 | * | 8/1995 | Milanovich ................. 433/7 |
| 5,904,479 | * | 5/1999 | Staples ....................... 433/7 |

FOREIGN PATENT DOCUMENTS

745098 * 2/1944 (DE) ........................................ 433/7
3241105-A * 5/1984 (DE) ........................................ 433/7

* cited by examiner

Primary Examiner—John J. Wilson
(74) Attorney, Agent, or Firm—Young & Thompson

(57) ABSTRACT

The invention relates to a suture expansion device. The suture expansion device comprises a central stretching screw support; on either side of the stretching screw support, a right and a left fixing means support for fixing to the right and, respectively, the left section of the jaw; and two stretching screws which are parallel to one another extending between the fixing means supports and accommodated in screw passages made in the stretching screw support and threaded to match the relevant stretching screw. The stretching screws can be screwed outwards in mutually opposed directions out of the stretching screw support in order to push the right-hand and left-hand fixing means supports apart. For each fixing means support a guide system is provided that prevents rotation of the relevant fixing means support relative to the stretching screw support and guides movement of the fixing means support in the longitudinal direction of the stretching screw. The stretching screws are freely rotatable about their longitudinal axes relative to the fixing means supports.

15 Claims, 2 Drawing Sheets

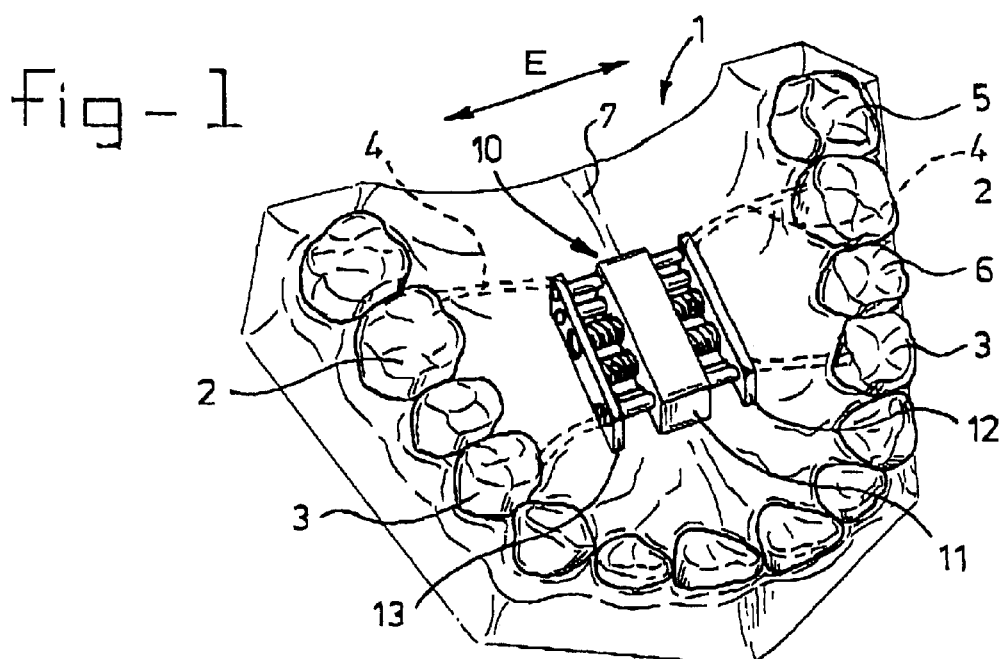
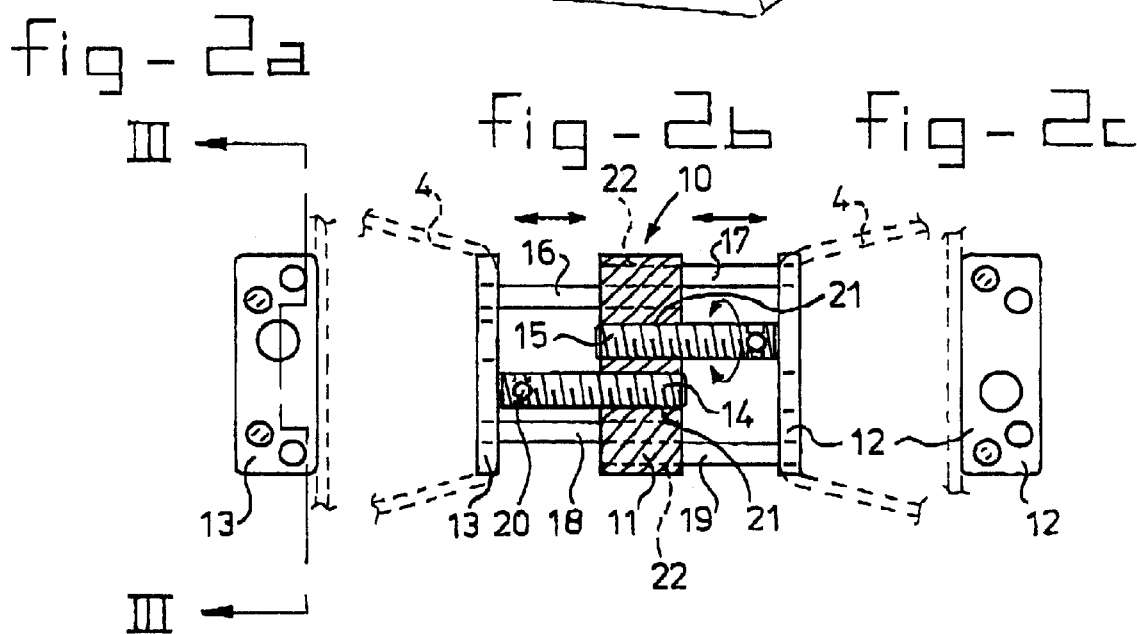
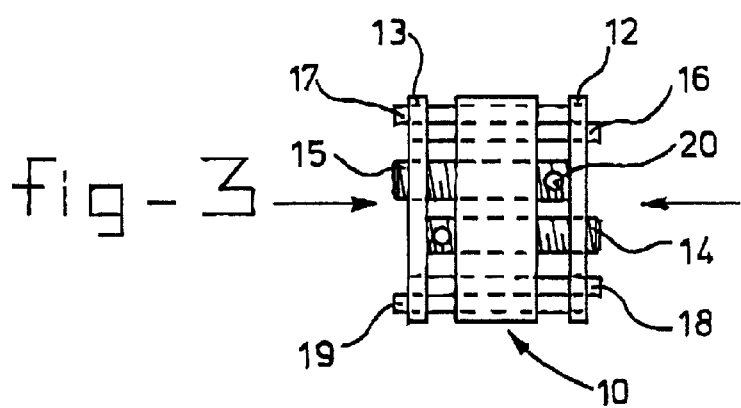

SUTURE EXPANSION DEVICE

The present invention relates to a suture expansion device comprising:
- a central stretching screw support;
- on either side of the stretching screw support, a right and a left fixing means support for fixing to the right and, respectively, the left section of the superior dental arch;
- two stretching screws, which are parallel to one another, extend between the fixing means supports and are accommodated in screw passages made in the stretching screw support and threaded to match the relevant stretching screw;

wherein the stretching screws can be screwed in mutually opposed longitudinal directions out of the stretching screw support in order to push the right-hand and left-hand fixing means supports apart.

In the specialist field suture expansion is also referred to as 'maxillary expansion' or 'palatal expansion', both of which terms are frequently prefixed by 'rapid'.

A suture expansion device of this type is disclosed in WO 94/26196. The suture expansion device known from this publication consists of a stretching screw support in the form of a cylindrical sleeve which is provided over virtually its entire length with a bore of large diameter provided with an internal thread and is provided at one end with a partition with a bore of small diameter, provided with an internal thread, therein. At one side a pin provided with an external thread extends from the outside through the small bore, which pin forms a first stretching screw, and at the other side a hollow pin with an external thread is screwed in from the outside, which hollow pin forms the second stretching screw. The cavity in the hollow pin is such that the first stretching screw fits in said cavity as it were in a telescopic manner. In the fully screwed-in position the first stretching screw and the second stretching screw are inserted one inside the other virtually completely in the sleeve-shaped stretching screw support. If the sleeve-shaped stretching screw support is now turned the stretching screws move outwards in opposing directions at either end as a result of their opposing threads. At their ends pointing away from the sleeve-shaped stretching screw support the stretching screws have fixing means supports in the form of U-shaped wires. The expansion length achievable with this suture expansion device is of the order of magnitude of 1.5 times the length of the suture expansion device in the fully screwed-in position. A significant disadvantage of this known suture expansion device is, however, that this device is insufficiently stable and rigid. Consequently, the jaws, or, more accurately, the right and the left portion of the superior dental arch, can also be pushed skew as well as, as intended, pushed apart. A further problem is that insofar as the device according to WO 94/26196 does have some rigidity and stability, this is provided only by the stretching screws, which has the associated risk of jamming.

The aim of the present invention is to provide a suture expansion device of the type with which the maximum expansion stroke has a length of the order of magnitude of approximately 1.5 (or possibly more) times the length of the suture expansion device measured in the expansion direction when the device is in the fully retracted position, which device is of particularly stable and rigid construction and is reliable in operation.

Said aim is achieved according to the invention in that for each fixing means support a guide system is provided that prevents rotation of the relevant fixing means support relative to the stretching screw support and guides movement of the fixing means support in the longitudinal direction of the stretching screw. The guide system provides the construction of the suture expansion device with rigidity and stability. The guide system ensures that while the fixing means supports are movable relative to the stretching screw support in the longitudinal direction of the stretching screws they in other respects remain fixed with respect to the stretching screw support.

Because two stretching screws which are effective in opposing directions are used, a relatively large expansion stroke can be achieved which will be in the order of magnitude of the sum of the lengths of the stretching screws.

To make the suture expansion device expand, the one stretching screw and the other stretching screw can be turned alternately, but it is also possible to unscrew first one stretching screw to its full extent and then the other stretching screw. In practice, incidentally, the expansion will take place gradually in the sense that the expansion increases by a predetermined extent per predetermined unit time. In this context it is possible, for example, to conceive an increase in the expansion of approximately 0.6 mm per day, an expansion step of approximately 0.2 mm, which can be achieved by, for example, unscrewing each expansion screw by 0.1 mm, being made in the morning, at midday and in the evening. If the screw threads are suitably chosen each screw can move out 0.1 mm on turning through 90°.

According to a preferred embodiment of the invention the stretching screws are freely rotatable about their longitudinal axes relative to the fixing means supports. By allowing the stretching screws to bear freely on the fixing means supports or at least keeping them freely rotatable about their own longitudinal axis relative to the fixing means supports, no moment will be exerted on the fixing means supports by turning the stretching screws and said fixing means supports will only be pushed outwards or, on screwing in, be able to move inwards, at least provided they are not restrained.

Although the guide system according to the invention can be implemented in a variety of ways, from the constructional, cost and reliability standpoint it is preferable if each guide system comprises at least one guide rod which is fixed by one end to the relevant fixing means support and which is accommodated in a guide passage in the stretching screw support such that it is slidable in the longitudinal direction. Such a guide system is compact and simple to produce.

With a view to, in particular, a robust, stable and rigid suture expansion device it is preferable according to the invention if each guide system comprises two of said guide rods, which are positioned some distance apart in a longitudinal direction running transversely to the left/right direction, and the stretching screws, viewed in said longitudinal direction, are located between the two guide rods. With this arrangement the guide rods provide the mutual stability and rigidity between the fixing means supports and the stretching screw support, whilst the stretching screws themselves are subjected to no or hardly any stress other than pressure, as a result of which, inter alia, jamming is largely prevented. Moreover, by positioning the stretching screws between the two guide rods it is possible largely to counteract the guide rods being able to jam in their guide passages in the stretching screw support as a consequence of forces acting transversely to the guide direction.

According to an advantageous embodiment, with this arrangement said longitudinal direction will run essentially parallel to the patient's palate when the suture expansion device is in the use position.

In order to obtain a suture expansion device which is is compact as possible in the fully retracted position and has as large as possible an expansion stroke in the fully expanded position, it is advantageous according to the invention if the stretching screws and guide systems extend from the right-hand to the left-hand fixing means support when the suture expansion device is in the retracted position. In order further to increase the compactness it is furthermore advantageous with this arrangement if the guide rod or guide rods and stretching screw belonging to the right-hand and left-land fixing means support respectively extend with their left-hand or right-hand end respectively into, or even through, the left-hand or right-hand fixing means support, respectively, when the device is in said position.

To prevent the suture expansion device being screwed too far apart it is advantageous according to the invention if, per fixing means support, a travel limiter prevents a predetermined maximum distance between the fixing means support concerned and the stretching screw support being exceeded. Otherwise it would be possible for a fixing means support to become completely detached from the stretching screw support, which would render the suture expansion device ineffective in its entirety and would give rise both to a great deal of discomfort for the patient and considerable work for the specialist treating the patient.

In order to be able to turn the stretching screws it is advantageous according to the invention if each stretching screw is provided with engagement means on which the tool is able to engage for turning the stretching screw concerned. According to an advantageous embodiment, the engagement means call comprise holes distributed around the circumference of the stretching screw, which holes are positioned preferably 90° or at most 90° apart. In this way an element suitable for the purpose can in each case be inserted in a hole and the stretching screw can then be turned a quarter turn so as to be able to insert the element concerned in the next hole. Because the engagement means are readily accessible at all times for engaging a tool therein it is advantageous according to the invention if the engagement means are provided at that end of the stretching screw concerned which faces in the unscrewing direction. With a view to the greatest possible compactness when the suture expansion device is in the fully retracted position it is preferable if the ends of the respective stretching screws provided with engagement means are recessed in an indent open at the bottom in the respective fixing means support on which the respective stretching screw acts during expansion. So as to be able to ensure expansion by an accurately predetermined value per turning stroke of a stretching screw with this arrangement, it is advantageous according to the invention if each indent open at the bottom is provided with sloping guide surfaces on either side, which guide surfaces enclose an angle equal to the angular distance between the holes and have an imaginary point of intersection above the holes, such that a rod- or pin-shaped tool can be inserted over the one guide surface into one of the holes. In this context top and bottom are related to the position when placed in the mouth. If the guide surfaces and holes are, for example, 90° apart and the stretching screw is turned such that two of the holes are located in the extension of the guide surfaces, a pin can be inserted over one of the guide surfaces into a hole and turned through 90° until it comes into contact with the other guide surface, which with this arrangement actually acts only as a stop face. During said turning the next hole comes into line with the one of the guide surfaces.

The present invention will be explained in more detail below with reference to two illustrative embodiments shown diagrammatically. In the drawing:

FIG. 1 shows a diagrammatic perspective view of a model of an upper jaw in which a suture expansion device according to a first illustrative embodiment of the invention has been placed;

FIGS. 2a, 2b and 2c show, respectively, a right-hand side view, a plan view and a left-hand side view of the suture expansion device according to FIG. 1, the plan view, which is shown partially in section, being in an expanded position but not yet in the maximum expanded position;

FIG. 3 shows a plan view of the suture expansion device according to FIGS. 1 and 2 in the fully retracted position;

Figure 4:
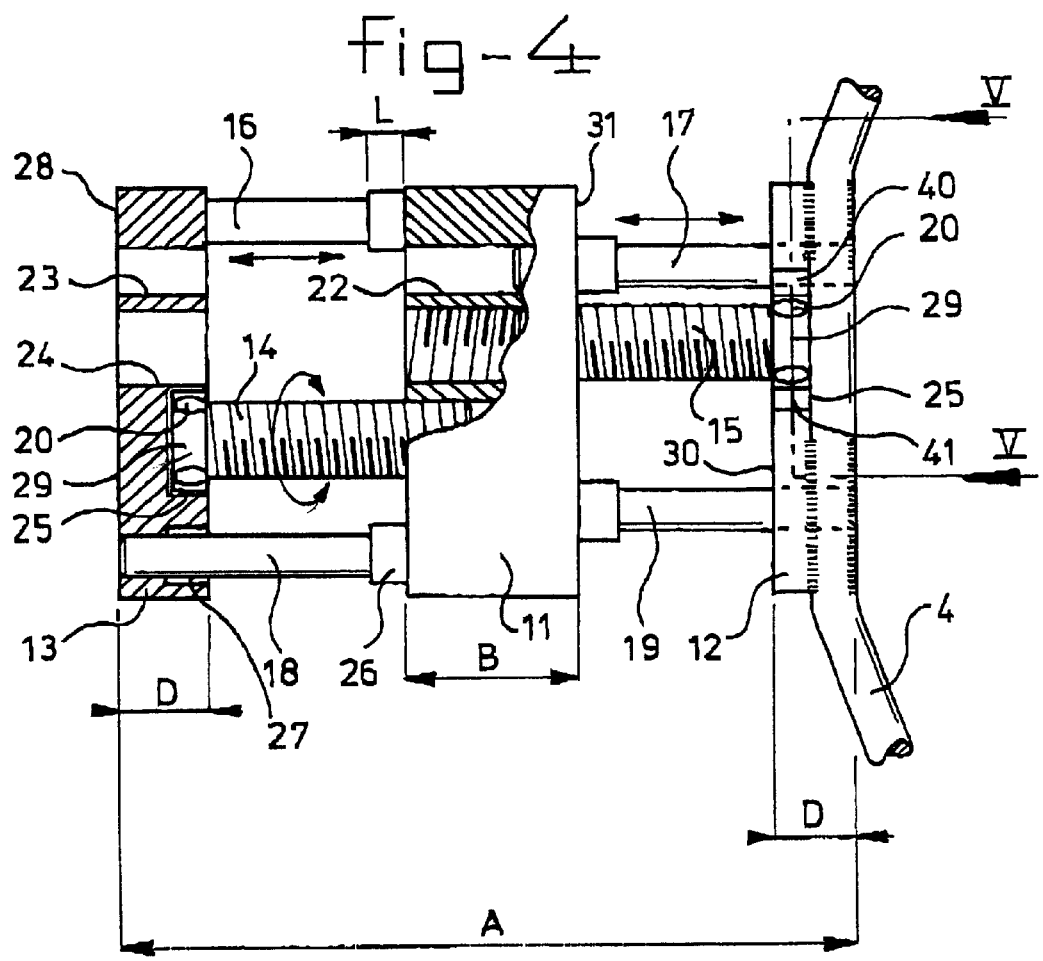
FIG. 4 shows a suture expansion device according to a second illustrative embodiment of the invention; in plan view, partial cross-section and not yet fully expanded position.

In FIG. 1 a model of the upper teeth is indicated by 1. A suture expansion device 10 according to the invention has been placed in this model, which suture expansion device 10 is attached by means of wires 4 and bands, which are not shown, at either side to a molar 2 and a premolar 3. It will be clear that it is also possible to make use of the rear molars 5 and/or rear premolars 6 instead of the front molars 2 and/or front premolars 3 for attaching the suture expansion device 10. By expanding the suture expansion device 10 in the left/right direction (double headed arrow E), the upper set of teeth can be spread, during which operation in general the so-called suture 7 will open.

With reference in particular to FIGS. 2 and 3, but also to FIG. 1, the suture expansion device 10 according to the first illustrative embodiment consists of a central stretching screw support 11 with, on either side, a left-hand fixing means support 12 and right-hand fixing means support 13. The suture expansion device 10 also comprises two stretching screws 14 and 15 which are parallel to one another, extend between the fixing means supports 12 and 15 and are each accommodated in a screw passage 21 made in the stretching screw support 11. Threading matching the thread of the stretching screws 14 and 15 is provided in said screw passage 21. Furthermore, a guide system 17, 19 and 16, 18, respectively, is provided per fixing means support 12, 13, which guide system prevents rotation of the fixing means support 12 or 13, respectively, relative to the stretching screw support 11 but allows movement of the respective fixing means support 12 or 13 in the longitudinal direction of the stretching screws 14, 15.

Each guide system consists of two guide rods 17, 19 and 16, 18, respectively, which are fixed by their one end to the fixing means support 12 or 13, respectively, and by their other end are slidably accommodated in a guide passage 22 formed in the stretching screw support 11.

So that it is possible to turn the stretching screws 14 and 15 it is important that these screws are not joined to the fixing means supports 13 and 12, respectively, such that they are unable to rotate. In the embodiment according to FIGS. 1, 2 and 3 the stretching screw 14 or 15, respectively, is not joined to the fixing means support 13 or 12, respectively, at all other than by bearing on said support under the influence of pressure.

The stretching screws 14 and 15 can be turned by placing a suitable tool in the holes 20 positioned 90° apart in the circumferential direction. As a consequence of the guide systems 17, 19 and 16, 18, hardly any moment will be exerted on the fixing means supports 12 and 13 on turning the stretching screws 14 and 15. The guide systems 17, 19, 16 and 18 also ensure, and this is very important, that the movement of the fixing means supports 12, 13 relative to the stretching screw support 11 is an essentially purely translational movement. In this way it is ensured that the front fixing points (the premolars 3 in FIG. 1) and the rear fixing points (the molars 2 in FIG. 1) are stressed to an equal extent during expansion.

The expanded position shown in particular in FIG. 2b is not the maximum expanded position. This maximum expanded position is achieved when the stretching screws 14 and 15 are unscrewed even further until they come completely free or virtually completely free from their passages 21. Preferably, the stretching screws 14 and 15 will still extend approximately 1 to 2 mm into the stretching screw support 11 in the maximum expansion position. In order to fix the maximum position and to prevent the screws coming out of the stretching screw support 11 completely, travel safety features can be provided on the stretching screws 14 and 15 or optionally on the guide systems 17, 19 and 16, 18. As far as, for example, the stretching screws 14 and 15 are concerned, such a travel safety feature can be obtained by providing only the starting section of the stretching screw passages 21 with internal screw thread and providing the free ends of the stretching screws 14 and 15 with, for example, a burr. As far as stretching screw passage 21 for stretching screw 14 is concerned, the first 1 to 2 mm, for example, of that end thereof facing towards the fixing means support 13 is provided with an internal screw thread and that end of the stretching screw 14 which faces towards the fixing means support 12 is provided with a burr. The maximum achievable expansion stroke is then, in particular, determined by, on the one hand, the length of the stretching screws 14 and 15 and, on the other hand, the width of the stretching screw support 11 measured in the longitudinal direction of the stretching screws 14 and 15. With this arrangement, the length of the stretching screws can, for example, be optimised by countersinking the free ends, that is to say the ends thereof which face away from the fixing means support with which the stretching screw concerned interacts, in the other fixing means support or by allowing them to extend through the latter, as can be seen in FIG. 3.

FIG. 4 shows a second illustrative embodiment of a suture expansion device according to the invention in the expanded position but not yet in the maximum expanded position. The suture expansion device shown in FIG. 4 is, in particular, further optimised with regard to, on the one hand, the maximum achievable expansion stroll and, on the other hand, the compactness in the fully retracted position.

Since the suture expansion device according to FIG. 4 in broad lines corresponds to that according to FIGS. 1–3, corresponding parts have been provided with corresponding reference numerals.

The fixing means supports 12 and 13 are each provided with a recess 25 in which the active head 29 of the respective stretching screw 14 or 15 can be accommodated. The head 29 of the respective stretching screw 14 or 15 is provided with holes 20, positioned 90° apart in the circumferential direction, in which a tool can engage. The recesses 25 are open not only in the direction of the stretching screw support 11 but also in the downward and/or upward direction, that is to say in the one or the other direction perpendicular to the plane of the drawing according to FIG. 4. The reason for this is to keep the heads 29 of the stretching screws accessible to the tool. Accommodating the heads 29 of the stretching screws in the recesses 25 makes it possible to allow the inner surfaces 30 of fixing means supports 12 and 13 to bear against the outer surfaces 31 of the stretching screw support 11 on either side without any gap between them when the stretching screws are in the fully retracted position. This is highly beneficial for the compactness in the fully retracted position. The lengths of the stretching screws and guide rods are chosen such that the free ends thereof, or at least the ends thereof, which face away from the fixing means support with which the stretching screw or guide rod interacts are, in the fully retracted position, flush with the outer surface 28 of the respective stretching screw support 12 or 13 with which they do not interact or optionally even protrude through said outer surface 28 with some protrusion length. It should be clear that the effective lengths of the stretching screws 14 and 15, on the one hand, and the effective lengths of the guide rods 16, 18, 17 and 19, on the other hand, will be essentially equal, at least in be case of optimisation of, on the one hand, the compactness in the fully retracted position and, on the other hand, the maximum expansion stroke.

By providing a guide bush 26 on the stretching screw support 11 per guide rod 16, 17, 18, 19, which guide bush extends the guide passage 22 in the direction of the fixing means support 12 or 13 to which the respective guide rod is fixed, and providing the respective fixing means support 12 or 13, opposite the respective guide bushes 26, with a widening 27 around the respective guide rod, in which widening the guide bush 26 can be completely accommodated, the maximum expansion stroke can be further increased for the same minimum length, viewed in the expansion direction in the fully retracted position. The guide bushes 26 make it possible to unscrew the stretching screws 14 and 15 completely or virtually completely from the stretching screw support 11. In this way the maximum achievable expansion stroke comes close to the sum of the lengths of expansion screws 14 and 15. Apart from increasing the maximum expansion stroke, the guide bushes 26 also contribute to the stability of the guide systems by extending the length of the guide passages 22.

Figure 5:
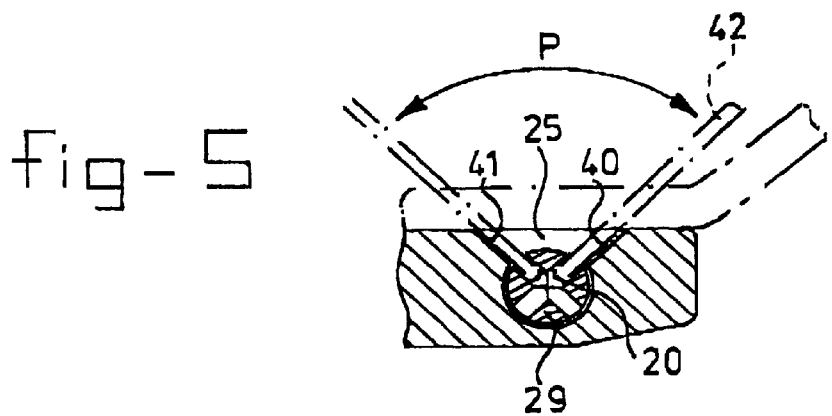
FIG. 5 shows a detailed cross-sectional view, corresponding to V—V in FIG. 4, of the inside of a fixing means support at the location of the indent for accommodating the operating end of a stretching screw.

To illustrate, on the one hand, the compactness in the fully retracted position and, on the other hand, the maximum expansion stroke in the fully expanded position, two examples are given below with reference to FIG. 4:

FIG. 5 is a cross-section corresponding to V—V in FIG. 4 and shows a cross-sectional detailed view of the inside of the fixing means support 12 at the location of the recess or indent 25 for accommodating the operating end 29 or head 29 of the stretching screw 15. The recess 25 is provided on either side with a sloping guide surface 40 and 41, respectively. Said guide surfaces 40, 41 enclose an angle of 90° between them, corresponding to the angular spacing between the holes 20 in the head 29 of the stretching screw. If a pin-shaped tool, indicated by 42, is now inserted over guide surface 40 into hole 20 and this tool is then turned in accordance with arrow P through 90° until it comes into contact with the other guide surface 41, then, on the one hand, angular rotation through the angle enclosed by the guide surfaces is reliably ensured and, on the other hand, it is ensured that the next hole is in line with the one guide surface 40 so as to be readily accessible to the tool 42 on the next rotational stroke. The recess or indent for the head 29 of the other stretching screw 14 is made in a corresponding manner.

Example 1

Thickness D of the fixing means supports 12 and 13 is: 2 mm;
Width B of the stretching screw support 11 is: 6 mm;
Length of stretching screws 14 and 15 and guide rods 16, 17, 18 and 19 is: 8 mm, which length is measured from the inner surface 30 of the fixing means support to which the screws are effectively joined.
In the fully retracted position the length A is then B+2D=10 mm.

Assuming that the free ends of the stretching screws 14 and 15 remain screwed 1 to 2 mm into the stretching screw support 11, for example in the case of the absence of the guide bushes 26, the length A in the case of full expansion is:

$$A = 2 \times D + B + 2 \times (\text{screw length} - 1 \text{ to } 2 \text{ mm}) = 22 \text{ to } 24 \text{ mm}.$$

The so-called expansion stroke is then 12 to 14 mm.

Example 2

Thickness D of the fixing means supports 12 and 13 is: 2 mm;
Width B of the stretching screw support 11 is: 6 mm;
Length of stretching screws 14 and 15 and guide rods 16, 17, 18 and 19 is: 8 mm, which length is measured from the inner surface 30 of the fixing means support to which the screws are effectively joined.
Length L of the guide bushes 26 is 1 mm.
In the fully retracted position the length A is then B+2D=10 mm.
On completely unscrewing the stretching screws 14 and 15 from the stretching screw support 11, the length A in the fully expanded position is then:

$$A = 2 \times D + 2 \times \text{screw length} = 26 \text{ mm}.$$

The maximum expansion stroke is then 16 mm. The maximum expansion stroke then has a length of 1.6 times the length of the suture expansion device in the fully retracted position measured in the expansion direction.

Although based on preferred illustrative embodiments, the examples given above are purely illustrative.

It should be clear that the dimensions cited can be varied depending on the circumstances. It is, for example, not only conceivable, but also possible, to increase the length A in the fully expanded position by reducing the thicknesses D and increasing the width B, for the same A in the fully retracted position. It is also possible, as will be immediately apparent, to increase the length A at maximum expansion and at the same time to increase the length A in the fully retracted position. With a view to unambiguity in operation of the stretching screws 14 and 15 it is preferable to provide these with mutually opposing thread.

What is claimed is:

1. Suture expansion device comprising:
   a central stretching screw support;
   on either side of the stretching screw support, a right and a left fixing means support for fixing to the right and, respectively, the left section of the superior dental arch;
   two stretching screws, which are parallel to one another, extend between the fixing means supports and are accommodated in screw passages made in the stretching screw support and threaded to match the relevant stretching screw;
   wherein the stretching screws can be screwed in mutually opposed longitudinal directions out of the stretching screw support in order to push the right-hand and left-hand fixing: means supports apart; and
   wherein for each fixing means support a guide system is provided that prevents rotation of the relevant fixing means support relative to the stretching screw support and guides movement of the fixing means support in the longitudinal direction of the stretching screw.

2. Suture expansion device according to claim 1, wherein the stretching screws are freely rotatable about their axes relative to the fixing means supports.

3. Suture expansion device according to claim 1, wherein each guide system comprises at least one guide rod which is fixed by one end to the relevant fixing means support and which is accommodated in a guide passage in the stretching screw support such that it is slidable in the longitudinal direction.

4. Suture expansion device according to claim 3, wherein each guide system comprises two of said guide rods, which are positioned some distance apart in A longitudinal direction running transversely to the left/right direction, and wherein the stretching screws, viewed in said longitudinal direction, are located between the two guide rods.

5. Suture expansion device according to claim 4, wherein said longitudinal direction runs essentially parallel to the patient's palate when the suture expansion device is in the use position.

6. Suture expansion device according to claim 1, wherein the stretching screws and guide systems all have essentially the same length.

7. Suture expansion device according to claim 1, wherein the stretching screws and guide systems extend from the right-hand to the left-hand fixing means support when the suture expansion device is in the retracted position.

8. Suture expansion device according to claim 1, comprising, per fixing means support, a travel limiter which prevents a predetermined maximum distance between the fixing means support concerned and the stretching screw support being exceeded.

9. Suture expansion device according claim 1, wherein each stretching screw is provided with engagement means on which a tool is able to engage for turning the stretching screw concerned.

10. Suture expansion device according to claim 9, wherein the engagement means comprise holes distributed around the circumference of the stretching screw, which holes are positioned 90° or at most 90° apart.

11. Suture expansion device according to claim 10, wherein the engagement means are provided at that end of the stretching screw concerned which faces in the unscrewing direction.

12. Suture expansion device according to claim 11, wherein the end of each stretching screw provided with engagement means is recessed in an indent open at the bottom in the respective fixing means support on which the stretching screw acts during expansion.

13. Suture expansion device according to claim 12, wherein the indent open at the bottom is provided with sloping guide surfaces on either side, which guide surfaces enclose an angle equal to the angular distance between the holes and have an imaginary point of intersection above the holes, such that a rod- or pin-shaped tool can be inserted over the one guide surface into one of the holes.

14. Suture expansion device according to claim 1, wherein a guide bush is provided in the extension of each guide rod passage, at the end thereof that faces towards the fixing means support to which the respective guide rod is fixed.

15. Suture expansion device according to claim 14, wherein the respective fixing means support is provided, around said respective guide rod, opposite the guide bush, with a widening in which the guide bush can be accommodated dated in its entirety.

* * * * *